United States Patent [19]
Hon

[11] Patent Number: 6,048,323
[45] Date of Patent: Apr. 11, 2000

[54] TRANSDUCER SUPPORT PLATE AND TOCODYNAMOMETER ATTACHMENT SYSTEM

[76] Inventor: Edward H. Hon, 11 Bradbury Hill Rd., Bradbury, Calif. 91010

[21] Appl. No.: 09/059,603

[22] Filed: Apr. 13, 1998

Related U.S. Application Data

[63] Continuation-in-part of application No. 08/720,694, Oct. 2, 1996
[60] Provisional application No. 60/004,694, Oct. 2, 1995, and provisional application No. 60/004,661, Oct. 2, 1995.

[51] Int. Cl.[7] .................................................. A61B 5/103
[52] U.S. Cl. ............................................................ 600/588
[58] Field of Search .................................... 600/587, 588, 600/591, 595, 459

[56] References Cited

U.S. PATENT DOCUMENTS

| | | |
|---|---|---|
| 4,696,307 | 9/1987 | Montgieux ............................ 600/534 |
| 4,920,966 | 5/1990 | Hon et al. ............................. 600/459 |
| 5,070,888 | 12/1991 | Hon et al. ............................. 600/591 |
| 5,394,877 | 3/1995 | Orr et al. .............................. 600/459 |

*Primary Examiner*—Max Hindenburg
*Assistant Examiner*—Pamela Wingood
*Attorney, Agent, or Firm*—Loeb & Loeb LLP; F. J. Far-hadian

[57] ABSTRACT

A device for receiving and holding a removable ultrasound transducer and a tocodynamometer against the exterior of the abdomen of the patient is disclosed. The device comprises an improved transducer support plate which is maintained in fixed contact with the abdomen of the patient by fastening pads, including an adhesive hydrogel and a belt encircling the patient to provide the necessary counterforces to the transducer support plate that is simple to attach and remove from a patient.

20 Claims, 4 Drawing Sheets

TRANSDUCER SUPPORT PLATE AND TOCODYNAMOMETER ATTACHMENT SYSTEM

RELATED APPLICATIONS

This application is a continuation-in-part of application Ser. No. 08/720,694 filed Oct. 26, 1996, which claims priority to U.S. provisional application Ser. No. 60/004,694 and U.S. provisional application Ser. No. 60/004,661, both filed on Oct. 2, 1995, all of which are incorporated by reference herein.

BACKGROUND OF THE INVENTION

1. Field of the Invention

The present invention is directed to a support plate for holding sensors, such as a transducer and a tocodynamometer, in selected relationship against the body of a patient.

2. Description of the Related Art

The present invention relates to apparatus for monitoring uterine contractions during pregnancy and throughout labor and delivery and an apparatus for ultrasound monitoring of a mother and the fetus. Information relating to the frequency, magnitude and pattern of uterine contractions is valuable to the physician, as a measure of the normal progression of labor. Additionally, it provides a guide for nurses and physicians in the use of medication or the need for other remedial actions.

The two types of apparatus most widely used at the present time for monitoring labor contractions are: (1) internal catheters inserted into the uterus to measure changes in the amniotic fluid pressure in the amniotic sac such as generally shown in U.S. Pat. No. 4,543,965 to Pack; and (2) external devices which consist of a pressure transducer held in place on the abdomen of the patient by a belt fitted around the waist of the patient such as generally shown in the U.S. Pat. No. 3,520,294 to Fuzzell, and external devices in which the pressure transducer is bound by a strong adhesive on the abdomen of the patient, such as disclosed in U.S. Pat. No. 5,070,888 to Hon et al.

The most reliable device for measuring uterine contractions is an internal type as it usually provides accurate data, but has a number of significant disadvantages which include:

1. The uterine cervix must be partially dilated and the amniotic sac ruptured.

2. During insertion of the catheter, bacterial and/or viral contaminants may be carried from the vagina and/or cervix into the uterine cavity and cause serious infection.

3. The catheter system may not be used where certain complications exist, e.g. uterine bleeding, here catheter insertion might cause additional bleeding; fever due to suspected uterine infection, in this case catheter insertion might exacerbate the situation.

4. If great care is not taken, during insertion of the catheter through its guiding tube, the lower segment of the uterus may be perforated.

5. Catheter insertion is uncomfortable for the patient and inconvenient and time consuming for the medical and nursing staff. Before insertion, a sterile area must be prepared around the vaginal orifice and then draped with sterile towels. The catheter, catheter guide, fluid filled syringe and pressure measuring apparatus then have to be assembled. The entire operation usually takes 7–10 minutes.

6. Even though great care is exercised during catheter insertion, it is possible for the catheter to become clogged with a blood clot or vernix caseosa during labor so that the recorded uterine contraction data is compromised, sometimes to the point where it is not usable, even though the catheter system has been flushed with sterile water. In this case, the catheter must be replaced and the entire insertion process repeated.

7. During attempted flushing it is possible to damage the expensive pressure transducer if the flushing fluid is inadvertently directed towards the pressure transducer rather than towards the catheter.

8. Uterine contractions are often not monitored in the delivery room because current catheter systems usually place the pressure transducer directly on the fetal monitor so that patient transfer from labor to delivery room requires the reconnection of the catheter system to another pressure transducer on another fetal monitor—an awkward and time-consuming process. Additionally, it is difficult to maintain catheter sterility during the transfer process.

One of the external types of apparatus presently used consists of a pressure transducer held in place against the patient's abdomen by an encircling belt without any other fixation means. The belt provides the counter-pressure which keeps the pressure transducer firmly against the maternal abdominal wall during contractions. Without it, the pressure transducer would merely ride up and down with each uterine contraction and hence would not reflect the changes in abdominal wall tension associated with uterine contractions.

While the external system using only an encircling belt to secure the transducer is simple and convenient to use and does not suffer from some of the major disadvantages of the internal system, it too has significant problems, which include:

1. Even under the best of conditions the overall quality of data obtained by external means secured only by a belt is not as precise as that obtained using an internal uterine catheter.

2. Uterine contraction data is easily compromised by fluctuations in belt tension which does not provide the necessary fixation forces to keep the transducer in a fixed relationship to the abdomen. If the labor is intense and the patient moves, belt tension changes continually. Hence for satisfactory operation, the patient must be kept relatively immobile. Once belt tension has been altered by patient movement, the belt tension must be readjusted, otherwise no uterine activity data will be recovered.

3. When the patient is transferred from the labor ward to the delivery room the belt tension has to be readjusted. Because this can be time consuming, it is not usually done so that the external technique is infrequently used in the delivery room.

4. Because of the foregoing problems, such external uterine activity monitoring techniques provide at the best a fragmentary record of uterine activity, even so, much of the data is of poor quality.

The second type of external system in which the transducer assembly is bonded directly onto the abdominal wall of the patient eliminates the fixation problems of the belt system, but was problematic because the removal of the transducer assembly was difficult and required the use of solvents to break the bond to the skin of the patient U.S. Pat. No. 5,070,888 to Hon et al. teaches the use of a strong adhesive on the abdomen of a patient that formed a solid bond with the skin in order to secure the transducer to the patient. Such an adhesive was sufficiently strong to maintain the transducer in place on the patient without the use of a belt. However, such a system was difficult to remove because the adhesive would bond to the skin of the patient and required the use of solvents for the removal of the transducer from the patient.

In the past, additional means other than a belt for fixing the external transducer to the patient's abdomen or bonding the external transducer to the skin of the patient have been attempted.

As long ago as 1932, in "Surgery, Gynecology and obstetrics," Vol. 55 (1932) at page 45, a tripod support assembly was disclosed which had an air transducer supported in a tripod-like structure which was fixed by tapes tied in ringlets of the tripod which was held fast by adhesive straps to a patient's loins. This structure was not widely employed and is not presently being used. In effect, this system conceptually was a precursor of the belt system.

Another prior art device disclosed in "Science 1947" at page 427 (shown diagrammatically in FIG. 6 thereof) consisted of a heavy brass ring (240 grams) held in place on the abdomen by double coated Scotch brand adhesive tape applied to the bottom side. A strain gauge was held in the center of each ring by a single lever system. This system was devised by Dr. Reynolds, but has never been widely used and is not in use at the present time.

The Reynolds device used doubled-sided adhesive tape to prevent lateral movement of the rings. The weight of the rings provided counter-pressure to hold the strain gauge against the abdomen during episodic changes in abdominal wall tension which occurs with uterine contractions. Since the operation of the device depended on gravitational forces to hold the strain gauge in correct relationship to the abdominal wall, it was mandatory that the patient be on her back and be relatively immobile during the use of the device.

There are a number of medical tests that require the monitoring of a patient, and in particular the monitoring of a mother and the fetus during pregnancy, with an ultrasound transducer, e.g. obtaining the fetal heartbeat, as well as a number of other conditions that cannot be observed directly. In use, a coupling gel is applied to the ultrasound transducer face and the ultrasound transducer is then moved over the area of the patient where the best data is obtained. The data is typically observed on a monitor, and/or is stored on hard storage media.

If data is to be obtained over a long period of time, some means of holding the ultrasound transducer in place is required. The transducer would need to be coupled in a fixed position with respect to the patient and the application of a counterforce to the transducer would be necessary to reflect changes in the abdominal wall tension associated with uterine contractions.

In the past, the means for holding an ultrasound transducer on a patient was accomplished by using an encircling abdominal belt, as is commonly used for holding a tocodynamometer in place during the measurement of contractions in order to provide the necessary counterforce on the transducer. However, such belts when used with an ultrasound transducer are difficult to keep in place because the transducer is not fixed to the patient. To function properly, the ultrasound transducer must be held in a fixed position once the belt has been tightened and locked. Since the surface of the maternal abdomen is not uniform or flat, it is sometimes difficult to fix the orientation of the ultrasound transducer at the optimum angle to obtain the fetal heartbeat. Because the tension of the belt system holds the transducer face essentially parallel to the maternal abdomen wall, it is sometimes difficult to obtain the required data, and it becomes necessary to change this parallel orientation by angulating the transducer face.

Further, the abdomen of the pregnant woman does not maintain a constant shape during the testing period. The movement of the fetus, as well as contractions, cause the shape of the abdomen to change. This change in shape of the abdomen alters the pressure on the belt, causing the belt to slip and change position, thereby also causing the ultrasound transducer to change its position. The required data is thus frequently lost or its reliability is compromised. The instability of a belt system demands constant checking by the nursing and medical staff to make sure that the ultrasound transducer has not moved significantly. Therefore, the use of a belt alone was not satisfactory for securing an ultrasound transducer to the abdomen of a patient because the belt could not provide the necessary fixation forces to fix the position of the transducer with respect to the patient.

In U.S. Pat. No. 4,920,966 to Hon et al., an adhesive layer was applied to the surface of a disc-shaped transducer base in contact with the skin. The adhesive formed a solid bond with the skin in order to secure the transducer to the patient. Such an adhesive was sufficiently strong to maintain the transducer in place on the patient without the use of a belt. However, such a system was difficult to remove because the adhesive would bond to the skin of the patient and required the use of solvents for the removal of the transducer from the patient.

Currently, tocodynamometer recording of uterine conditions is done with a belt enveloping the maternal abdominal wall to hold the tocotransducer in place. Unfortunately, the roughly cylindrical nature of the maternal anatomy coupled with patient movements makes it difficult to obtain satisfactory uterine activity records, especially in late labor.

Therefore, there exists a need for a transducer holder in which the proper fixation and counterforces can be applied to the transducer that is simple to attach and remove from the patient.

SUMMARY OF INVENTION AND OBJECTS

The present invention is directed to an external device for supporting a combination transducer assembly for measuring the frequency, magnitude and pattern of uterine contractions during labor and for supporting an ultrasound transducer for monitoring a fetus and mother during pregnancy. The combined ultrasound transducer and tocodynamometer of the present invention comprises an improved transducer support plate which is maintained in fixed contact with.the abdomen of the patient by fastening pads, including an adhesive hydrogel and a belt encircling the patient to provide the necessary counterforces to the transducer support plate that is simple to attach and remove from a patient. The transducer support plate of the present invention is adapted to receive and hold a removable sensor against the abdomen of the patient.

A hydrogel layer is present on the lower surface of the fastening pads for attachment to the patient. The hydrogel is a mild adhesive which is sufficiently strong to provide the necessary fixation forces to fix the transducer support plate on the patient, but does not form a strong bond with the skin of the patient. The hydrogel is easily removed from the skin of the patient without the use of solvents.

The encircling belt, when placed around the abdominal wall of the patient and tightened, provides the necessary counterforces to any movement in the abdominal wall caused by uterine contraction or movement of the patient. The combination of the encircling belt and the use of the hydrogel results in a stable attachment of the transducer support plate to the patient. The fastening pads may be made of a flexible material such as foam and act as a shock absorber for the support plate against the abdominal wall and are removably attachable to the transducer support plate.

The transducer support plate comprises a support base that is concave for adapting to the shape of the abdomen. The support base has an opening to support a housing for a sensor, which is typically a pressure transducer, such as a tocodynamometer that is held firmly against the abdomen of the patient. Other sensing devices can also be used, as known in the art. The pressure transducer may be integrally formed with the base or removably attached to the base. The signal output of the transducer is connected by wires to a conventional amplifying and recording means.

Alternatively, the pressure transducer may be fixed in a housing which is removably affixed to the support base so that the pressure transducer and its housing can be separated from the support base and the support base discarded after use, thereby permitting a sterile support base to be brought into contact with the patient's skin with each use. A flexible membrane is fitted across the active surface of the transducer such that the active surface of the transducer does not actually come into contact with the abdomen, thereby maintaining the transducer in a clean condition and at the same time preventing contamination of the sensor by any preparatory material used in maintaining the support base on the abdomen.

In the preferred embodiment, an isolation ring surrounds the active surface of the transducer thereby isolating and confining a portion of the abdominal wall tissue. The transducer measures the pressure changes in this confined portion of tissue which, because of its relative isolation from the other parts of the maternal abdominal wall tissue, is less subject to patient movement. As a result, the device of the present invention permits more accurate measurements of uterine contractions than available with prior existing external contraction sensing devices.

The support plate also provides for holding an ultrasound transducer in fixed position with respect to the patient and provides the necessary counterforces to the ultrasound transducer that is simple to attach and remove from the patient. The support plate of the present invention comprises an ultrasound transducer holding member made of a relatively rigid material having an opening conforming to the periphery of the ultrasound transducer.

The support plate of the present invention eliminates transducer instability problem, by positioning a tocotransducer at one end of the supporting platform. Since this system is firmly attached to the abdominal wall with a hydrogel adhesive and encircling belt, the tocotransducer is held in position throughout labor and thereby produces good records of uterine activity. The use of this combination makes all current maternal-fetal monitors obsolete, and does away with a need for a fetal electrode for the electrocardiogram and for measuring intrauterine pressure.

Therefore, the support plate is non-invasive and permits concurrent observation of the fetal life support system in the sense of the mother's cardiovascular system and the fetus' well being. If an abnormality in the fetal heart rate pattern is obscure, it can be checked against maternal status. And if the maternal status, that is the cardiovascular status is okay, then it is very unlikely that the abnormality in fetal heart rate pattern means anything. On the other hand, if the maternal cardiovascular system is compromised, and it shows a trend over time, and the fetus shows also a trend in fetal heart rate pattern, this makes the diagnosis of so-called "fetal distress" much more solid. The present invention provides a great advantage in guiding the management of patients, particularly avoiding unnecessary caesarian section for suspected fetal distress, which in fact may not exist.

OBJECTS OF THE PRESENT INVENTION

It is the object of the present invention to provide a continuous measurement of uterine contractions which is sufficiently accurate to provide a sound basis for patient management, yet at the same time not have the disadvantages inherent in an internal catheter system which have been cited previously.

It is a further object of this invention to provide a simple convenient method of more quickly attaching the device to the patient without causing patient discomfort.

It is a further object of this invention to provide a device that continually measures contractions more reliably than current existing external devices.

It is another object of the present invention to permit monitoring contractions without interfering with the patient's movement.

It is yet another object of the present invention to provide a monitoring device which is less expensive than existing contraction monitoring devices.

It is an object of the present invention to provide a means for attaching an ultrasound transducer to a patient that is more reliable and easier to use than existing devices.

It is another object of the present invention to provide a means for attaching an ultrasound transducer to a patient that will permit data to be obtained while the patient is moving.

It is still another object of the present invention to provide a means for attaching an ultrasound transducer to a patient that will permit the position of the ultrasound transducer to be maintained easily and reliably in a fixed position.

It is yet another object of the present invention to provide a means for attaching an ultrasound transducer to a patient that is simple to apply and use.

These and other objects of the present invention will be evident from the specification, claims and accompanying drawings.

DETAILED DESCRIPTION OF THE INVENTION

Figure 1:
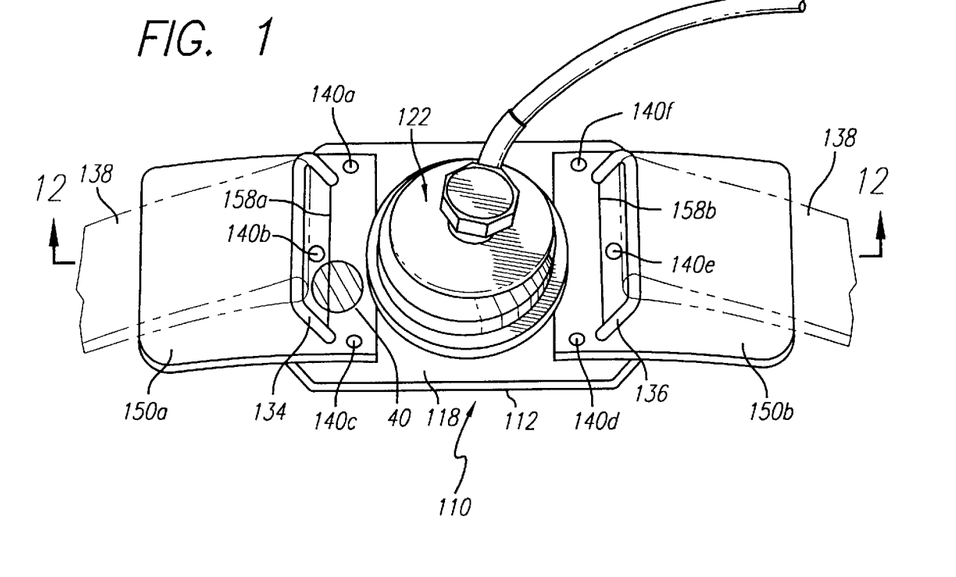
FIG. 1 is a top perspective view of the transducer support plate of the present invention with an ultrasound transducer, a pressure transducer, and fastening pads in place and with an encircling belt attached to the support plate.
Figure 2:
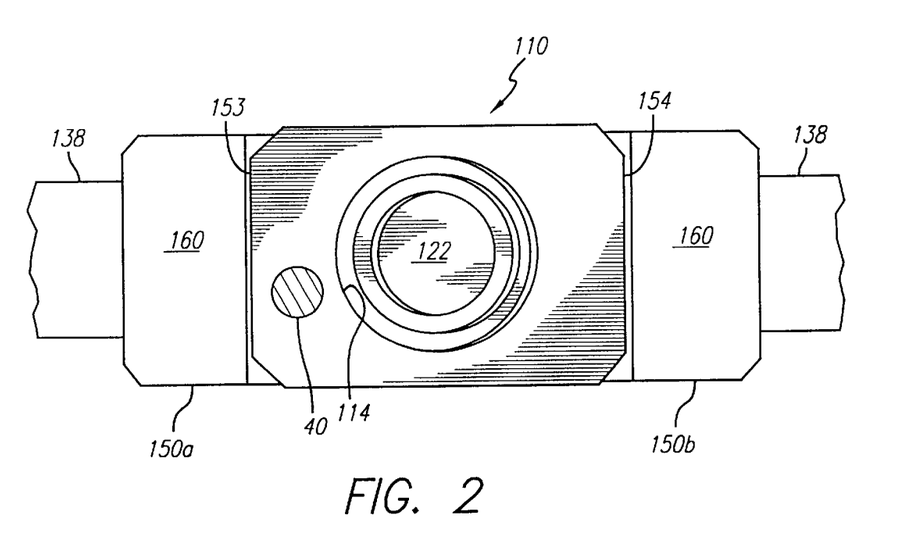
FIG. 2 is a bottom plan view of the transducer support plate of the present invention shown in FIG. 1.

Referring to FIGS. 1 and 2, a transducer support plate 110 is shown having a central ultrasound transducer holding member 112 and a pressure transducer 42, such as a tocodynamometer. The transducer support plate 110 is substantially rectangular and is made of a relatively rigid material such as polyvinyl chloride (PVC). The holding member 112 has a first accessing means 114, preferably in shape of a circular opening therein for receiving an ultrasound transducer 22 described below. Holding member 112, further comprises a second accessing means 40, preferably in form of a circular opening for receiving a pressure transducer assembly 42, also described below. The transducer support plate 110 has a slightly concave shape so as to assist in conforming the transducer support plate 110 to the shape of the abdomen of the patient.

Figure 4:
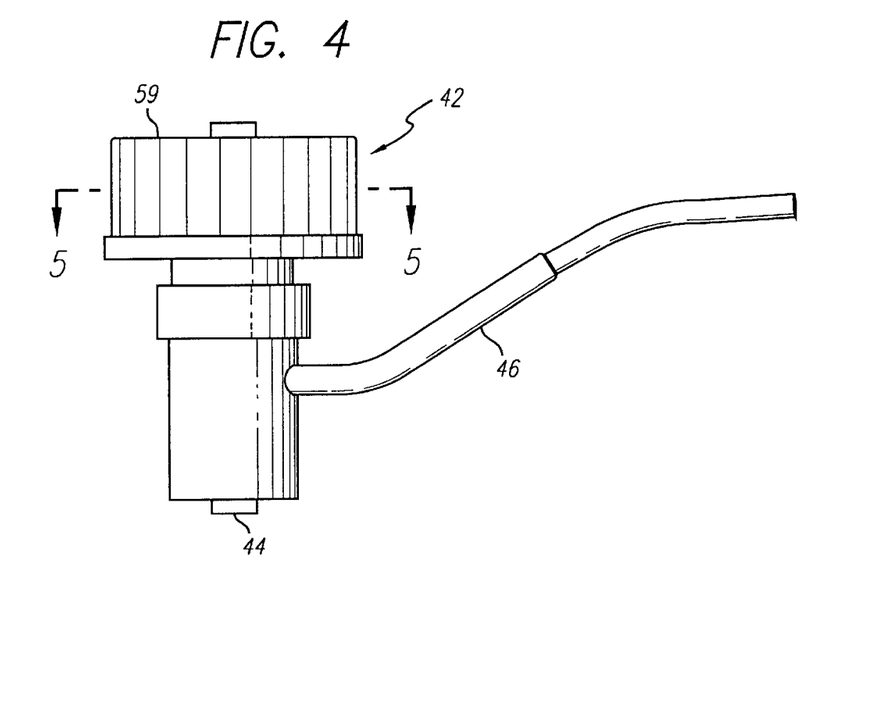
FIG. 4 is a side elevational view of pressure transducer for uterine activity monitoring.
Figure 5:
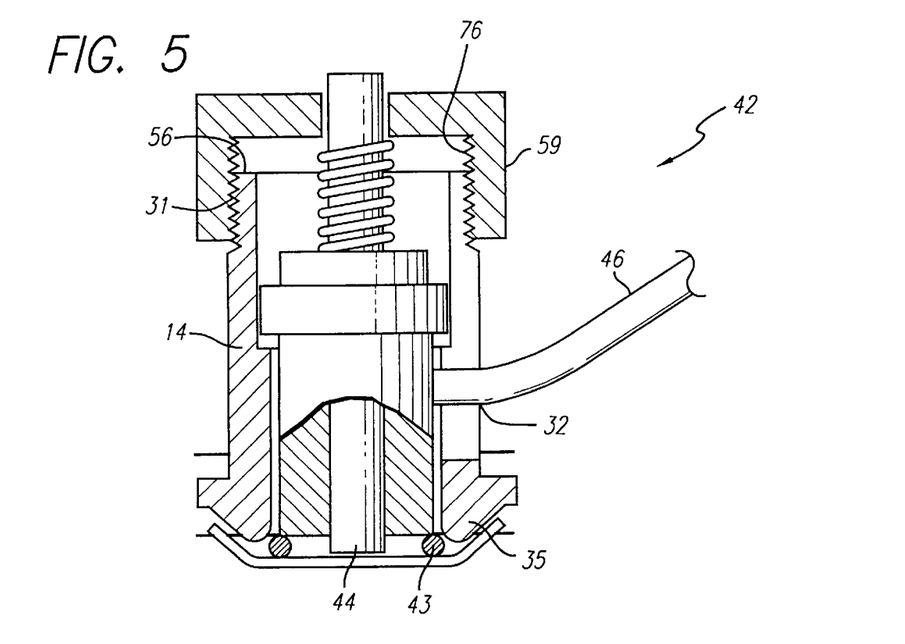
FIG. 5 is a side sectional view of a pressure transducer taken along lines 5—5 of FIG. 4.
Figure 7A:
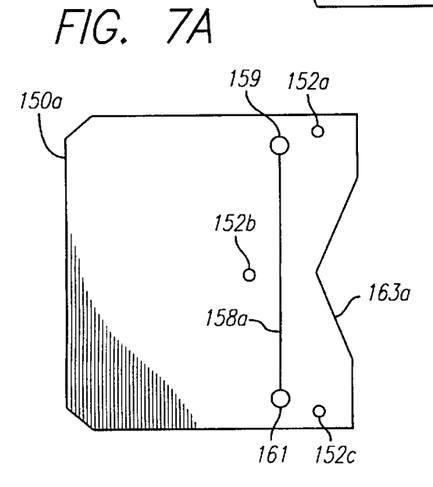
FIGS. 7A and 7B are top plan views of the fastening pads of the present invention used to fix the transducer support plate to the abdomen of a patient.
Figure 7B:
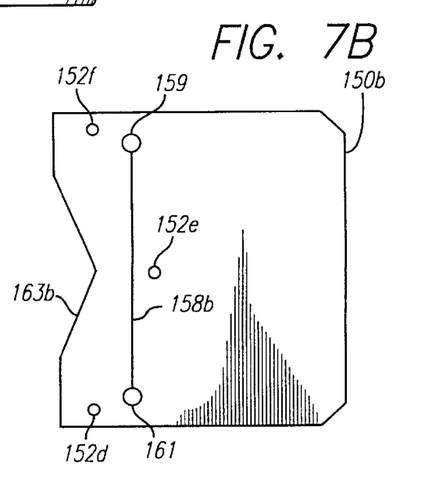

Referring to FIG. 4 and 5, a pressure transducer assembly 42 is shown comprising a transducer (e.g., a conventional, commercially available transducer such as sold by Transamerica Delaval, Inc.) which measures pressure applied to its active surface 44. The transducer 40 is suitable for measuring the face of uterine contractions when applied to the abdomen of a patient. Electrical lead wire 46 from the transducer 42 provides an electrical output signal response to the pressure applied to the active surface 44. The detailed structure of the transducer assembly 42 is disclosed in U.S. Pat. No. 5,070,888 issued to Hon et al. on Dec. 10, 1990 and is incorporated herein by reference.

In assembly, the transducer assembly 42 within the cylindrical hollow tubular fitting 14 with the wire 46 passing through the slot 32 in the side wall of the hollow tubular fitting 14. Shoulder 52 of the retaining structure 48 fits above shoulder 56. The pressure adjusting assembly 70 is then fitted within the cylindrical hollow tube 14. The pressure adjusting assembly 70 has its external thread 76 engaged in the internal threads 31 of the hollow tubular fitting 14. The pressure adjusting assembly is turned until the desired pressure on the transducer is achieved.

Surrounding the active end 44 of the transducer 42 and projecting slightly below the active surface 44 is an isolation ring 43 which serves to accentuate and stabilize the transference of internal pressure, isolating the surface area from extraneous vibrations.

Figures 8, 9, 10:
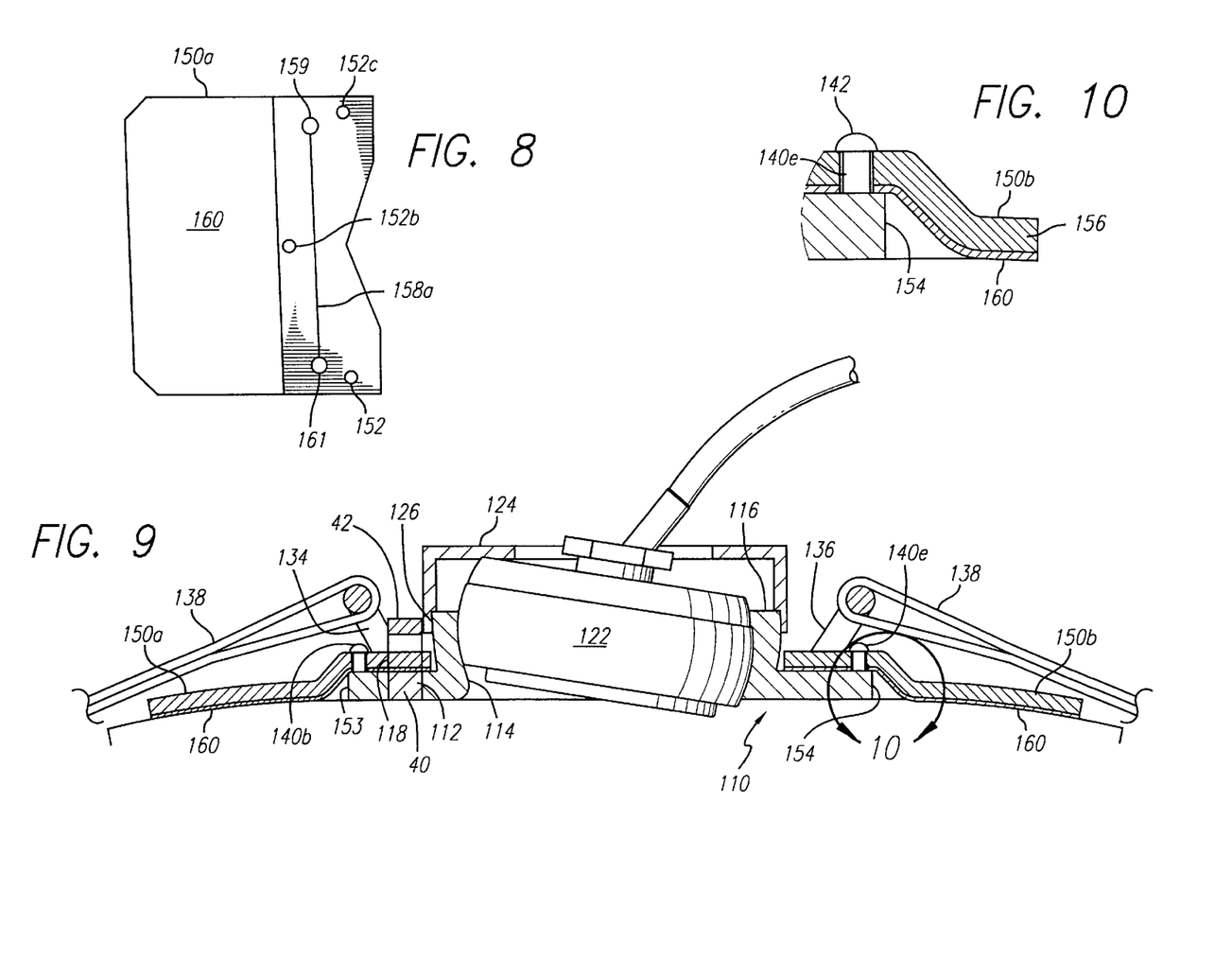
FIG. 8 is a bottom plan view of the fastening pad of FIG. 7A showing the hydrogel adhesive layer.
FIG. 9 is a side sectional view of the support plate taken along lines 9—9 of FIG. 1.
FIG. 10 is an enlarged sectional view along line 10 of FIG. 9 illustrating the attachment of the fastening pad to the support plate of the present invention.

Referring to FIG. 9, a sectional view of the transducer support plate 110 is shown. The transducer support plate 110 has a ring 116 surrounding the opening 114 and rising slightly above the top surface 118 of transducer support plate 110. In the preferred embodiment, the ring 116 is semi-flexible and functions to hold the ultrasound transducer 122 at a desired angle with respect to the abdomen of the patient.

In the preferred embodiment, a collar 124 that attaches to the periphery of the ring 116 may be employed for holding the ultrasound transducer 122 to maintain the ultrasound transducer 122 in position within the holding member 112. In the preferred embodiment, the collar 124 threads onto the ring 116 which has threads 126 on the exterior surface of the ring 116 of the holding member 112. The holding member 112 together with the transducer 122 forms a ball and socket arrangement as shown in FIG. 112. The ultrasound transducer 112 is friction fitted into the opening 114 of the holding member 112 and may be rotated in three degrees of freedom to the desired orientation. Once in the proper orientation, the collar 124 is employed to hold the ultrasound transducer 122. Also, the shape of the inside wall of the central support member may be curved so as to conform to the outside surface of the ultrasound transducer 122 and still be able to be easily inserted into the opening 114.

It is appreciated that instead of a collar 124 to hold the ultrasound transducer 122, any other means for holding the ultrasound transducer 122 such as the grasping members disclosed in U.S. Pat. No. 4,920,966 issued to Hon et al. on May 1, 1990, incorporated herein by reference, may be employed. Also, it is appreciated that the transducer support plate 110 may comprise a holding member 112 that maintains the ultrasound transducer 122 in a fixed position, without departing from the scope of the present invention.

In the preferred embodiment, the relatively rigid central holding member 112 is attached at its periphery to the relatively flexible transducer support plate 110 by conventional molding operation. It is appreciated that the entire transducer support plate 110 may be made of a relatively hard plastic, such as PVC, without departing from the scope of the present invention.

Figures 3, 6:
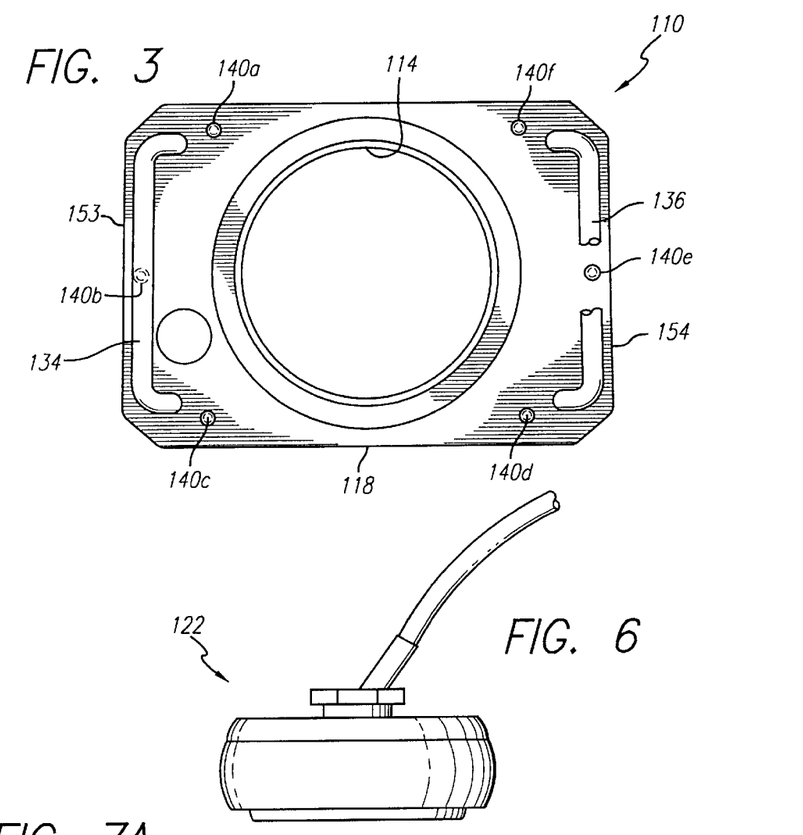
FIG. 3 is a top plan view of the transducer support plate of the present invention.
FIG. 6 is a side elevational view of an ultrasound transducer.

Referring to FIGS. 1, 3 and 9, extending above the upper surface 118 of the transducer support plate 110 are loop members 134 and 136 for attachment to the ends of a belt 138 used for encircling the patient to hold the transducer support plate 110 in place against the patient's abdomen. In the preferred embodiment, the loop members 134 and 136 are relatively rigid, are made of the same material as the transducer support plate 110 and can be molded to the transducer support plate 110. The belt 138 provides the necessary counter forces to keep the ultrasound transducer 122 firmly against the maternal abdominal wall during ultrasound monitoring of the patient.

The belt 138 provides the couterforces which keep the transducer 42 positioned firmnly against the maternal abdominal wall during the monitoring of the uterine contractions of a patient. Without the belt 138, the transducer would merely ride up and down with each uterine contraction and hence would not reflect the changes in abdominal wall tension associated with uterine contractions.

Referring to FIGS. 1, 3, 7A, 7B and 9, also, extending from the upper surface 118 of the plate are a plurality of pins 140a–f for engaging corresponding holes 152a–f in fastening pads 150a and 150b used for fixing the transducer support plate 110 to the abdominal wall of a patient described in detail below. Each of the pins 140a–f has a rounded head 142 to facilitate the insertion on the pins 140a–f into openings 152a–f of the fastening pads 150a and 150b as shown in FIGS. 6A and 6B. The rounded head 142 may have a larger diameter than the remainder of the pins 140a–f and a larger diameter than the holes 152a–f in order to lock the fastening pads 150a and 150b to the transducer support plate 110 once they are inserted over the pins 140a–f. The pins 140a–f are made of the same material as the transducer support plate 110 and can be molded as part of the plate 110 during manufacture.

Referring to FIGS. 1, 3, 7A, 7B, and 8, the fastening pads 150a and 150b have a width that corresponds to the width of the transducer support plate 110 and a length that extends beyond the length of the transducer support plate 110. In the preferred embodiment, the fastening pads 150a and 150b extend approximately 2 inches from each end 153 and 154 of the transducer support plate 110. Each of fastening pads 150a and 150b has a slot 158a and 158b, respectively, corresponding in position to the loop members 134 and 136, respectively, on the transducer support plate 110. The loop members 134 and 136 may pass through the slots 158a and 158b, respectively, as the fastening pads 150a and 150b are placed over the transducer support plate 110 and holes 152a–f engage the pins 140a–f. When the fastening pads are placed over the transducer support plate 110, the slots 156a and 156b and the holes 152a–f align with loop members 134 and 136, and pins 140a–f, respectively, and function to secure the fastening pads 150a and 150b to the transducer support plate 110. The slots 158a and 158b of the fastening pads 150a and 150b each have rounded enlarged ends 159 and 161 for accommodating the diameter of the loop members 134 and 136. The fastening pads 150a and 150b have and internal edge 163a and 163b, respectively, configured to fit around the holding member 112.

Referring to FIGS. 8 and 9, each of the fastening pads 150a and 150b comprises of a first layer of a flexible material, such as foam 156 and has a second layer of a mild adhesive, such as a hydrogel 160, which is applied to the lower surface of the foam layer 156 of the fastening pads 150a and 150b. The hydrogel 160 sticks the fastening pads 150a and 150b to the skin of the abdominal wall to fasten the transducer support plate 110 to the patient. A medical grade hydrogel 160, is commercially available from the 3M Company, and comprises a mild adhesive that is strong enough to maintain the transducer support plate 110 in a fixed position, yet does not form a solid bond with the skin of the patient. The hydrogel 160 provides the necessary fixation forces to support the transducer support plate 110 against the abdomen of the patient. A protective removable paper covering (not shown) may cover the hydrogel 160 until such time as it is desired to use the device.

The encircling belt 138 when placed around the abdominal wall of the patient and tightened provides the necessary counterforces to any movement in the abdominal wall caused by uterine contraction or movement of the patient. The hydrogel 160 provides the necessary fixation forces to keep the transducer support plate 110 in a fixed position with respect to the patient's abdominal wall. The combination of the encircling belt 138 and the use of the hydrogel 160 results in a stable attachment of the transducer 122 to the patient. The flexibility of the fastening pads 150a and 150b acts as a shock absorber for the transducer support plate 110.

In the preferred embodiment of the present invention, the transducer support plate 110 has a length of approximately 6 inches, and a width of approximately 4 inches. The circular opening 114 in the holding member 112 is approximately 2 ½ inches in diameter, only slightly larger than the diameter of a standard ultrasound transducer used in the United States such as sold by Corometrics, Inc. The precise size of the opening will depend on the diameter of the ultrasound transducer desired to be used with the device. The size of the transducer support plate 110 is sufficiently large to accommodate the distortions in the abdomen of the patient and still provide a stable base for the ultrasound transducer. It is appreciated that the transducer support plate 110 may have any other size or configuration suitable for its intended purpose.

In using the ultrasound transducer, a singular sequence of preparatory steps usually used with an ultrasound transducer are used. The location of the fetus is determined by conventional means. The adhesive protective layer is removed from the fastening pads 150a and 150b of the transducer holder plate 110 and it is then applied to the location where it is desired to hold the ultrasound transducer 122. A small amount of ultrasonic coupling gel is then applied to the face of the ultrasound transducer 122 and the ultrasound transducer 122 is then placed in the opening 114 in the holder and reoriented until the strongest signal is observed on the monitor. The collar 124 is then attached and turned to press against the outer periphery of the ultrasound transducer, thereby holding the ultrasound transducer 122 in a fixed orientation in relation to the patient. The encircling belt 138 is then tensioned about the patient to provide the appropriate counterforces to the transducer support plate 110.

While the transducer support plate 110 is in place, it is possible for the patient to move, walk around and to even exercise enough so as to be subjected to an exercise stress test (a highly desirable test).

The transducer assembly 42 is then fitted within the hollow tubular fitting 14 so that the active face of the transducer 44 and the isolation ring 43 is in contact with the flexible membrane 22 which is pressed against the abdomen. The lead wire 46 is then connected to the recording device 48 and the member 72 is then put in place and tuned Accordingly the isolation ring 43 and the active element 44 are of the transducer pressed against the abdomen of the patient through the membrane 22.

The pattern of the contractions may now be observed on the recording apparatus. The transducer assembly can be removed from the support base 12 at any time, leaving the support base 12 in place. Thus, the patient can be moved from one location to another by disconnecting the lead wire 46 from the recorder or by removing the transducer assembly 42. The transducer support plate 10 remains in place since the hydrogel 52 in combination with the belt 30 are sufficiently strong to form a fixed base relative to the skin of the patient. The coupling formed between the abdomen and the support base is sufficiently strong to prevent the lifting of the support base 12 when subjected to the downward pressure of the transducer assembly 42. Further, the monitoring apparatus can be used, without adjusting the base line of the recording apparatus, whether the patient is lying down or standing up.

When it is desired to remove the ultrasound transducer 122, the collar 124 is unscrewed so as to release the ultrasound transducer 122 for removal. The transducer support plate 110 is then removed from the patient by unfastening the encircling belt 138 and lifting the transducer support plate 110 away from the patient's abdomen. As the hydrogel 160 is a mild adhesive, no solvents are necessary to remove the plate from the patient's skin.

While the present invention has been described in detail with regards to the preferred embodiments, it is appreciated that other variation of the present invention maybe devised which do not depart from the inventive concept of the present invention.

What is claimed is:

1. An apparatus for supporting at least two transducer assemblies against the body of a patient, comprising:

a support plate having an upper surface and a lower surface adapted for placement against the body of a patient, said support plate having first and second accessing means for providing access to the body of a patient from said upper surface and through said support plate;

first support means for supporting a first transducer assembly relative to said support plate and in communication with said first accessing means, said support means holding the active end of said first transducer assembly proximate to the body of the patient when said lower surface is placed against the body of a patient;

second support means for supporting a second transducer assembly relative to said support plate and in communication with said second accessing means, said support means holding the active end of said second transducer assembly proximate to the body of a patient when said lower surface is placed against the body of a patient;

means for providing counterforces generally perpendicular to said upper surface and to position said support plate firmly against the body of a patient; and means for fixing said support plate in a fixed position with respect to the body of a patient.

2. The apparatus of claim 1 in which said first support means comprises a hollow tubular member in communication with said accessing means.

3. The apparatus of claim 2 in which said hollow tubular member has a support base extending through said accessing means to said lower surface of said support plate.

4. The apparatus of claim 3 in which said support base has a concave bottom surface for placement against the body of a patient.

5. The apparatus of claim 1 in which said second support means includes means for holding an ultrasound transducer assembly at selected angles relative to said support plate.

6. The apparatus of claim 5 including means for locking a transducer assembly at a selected angle relative to said support plate.

7. The apparatus of claim 1 in which said holding means is capable of removably holding a transducer assembly.

8. The apparatus of claim 1 in which said support plate is flexible.

9. The apparatus of claim 1 in which the said bottom surface of said support plate is concave to conform to the curvature of the abdomen of a patient.

10. The apparatus of claim 1 including a protective membrane for covering the active end of a transducer assembly, said protective membrane being positioned between the active end of the transducer assembly and the body of the patient.

11. The apparatus of claim 1 in which the transducer assembly being supported by said second support means is an ultrasound transducer for monitoring the activity of a fetus and patient during pregnancy.

12. The apparatus of claim 1 in which said second transducer is a pressure transducer for monitoring uterine contractions of a patient.

13. The apparatus of claim 1 in which said means for providing counterforces comprises an attachment means for attaching said plate to a belt for encircling the abdomen of a patient.

14. The apparatus of claim 13 including a belt for encircling the abdomen of a patient.

15. The apparatus of claim 1 further comprising at least one fastening pad for placement between said lower surface of said support plate and the skin of a patient.

16. The apparatus of claim 15 including coupling means for coupling said at least one fastening pad to said support plate.

17. The apparatus of claim 15 in which said at least one fastening pad includes a mild adhesive layer for adhering to the skin of the patient.

18. The apparatus of claim 1 in which said mild adhesive layer comprises a hydrogel material.

19. The apparatus of claim 15 in which said at least one fastening pad comprises a flexible material.

20. The apparatus of claim 19 in which said flexible material is foam.

* * * * *